United States Patent
Zee et al.

(10) Patent No.: US 10,052,305 B2
(45) Date of Patent: Aug. 21, 2018

(54) LIPOIC ACID AND DERIVATIVES THEREOF FOR THE TREATMENT OF CYSTINURIA

(71) Applicant: Buck Institute for Research on Aging, Novato, CA (US)

(72) Inventors: Tiffany Zee, Oakland, CA (US); Marshall L. Stoller, San Francisco, CA (US); Pankaj Kapahi, Kensington, CA (US)

(73) Assignee: BUCK INSTITUTE FOR RESEARCH ON AGING, Novato, CA (US)

( * ) Notice: Subject to any disclaimer, the term of this patent is extended or adjusted under 35 U.S.C. 154(b) by 0 days.

(21) Appl. No.: 15/284,318

(22) Filed: Oct. 3, 2016

(65) Prior Publication Data

US 2017/0112804 A1  Apr. 27, 2017

Related U.S. Application Data

(60) Provisional application No. 62/238,617, filed on Oct. 7, 2015.

(51) Int. Cl.

| | |
|---|---|
| *A61K 31/381* | (2006.01) |
| *A61K 31/19* | (2006.01) |
| *A61K 45/06* | (2006.01) |
| *A61K 9/00* | (2006.01) |
| *A23L 33/10* | (2016.01) |
| *A23K 20/10* | (2016.01) |
| *A23K 20/121* | (2016.01) |

(52) U.S. Cl.
CPC ............ *A61K 31/381* (2013.01); *A23K 20/10* (2016.05); *A23K 20/121* (2016.05); *A23L 33/10* (2016.08); *A61K 9/0056* (2013.01); *A61K 31/19* (2013.01); *A61K 45/06* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 6,331,559 B1 | 12/2001 | Bingham et al. | |
| 2008/0020995 A1* | 1/2008 | Purpura | A61K 8/4986 514/58 |

FOREIGN PATENT DOCUMENTS

WO    WO 2003/084532 A1    10/2003

OTHER PUBLICATIONS

Jayanthi et al. In Biochemistry International (1991), 25(1), 123-126).*
J. G. Cannon Chapter Nineteen in Burger's Medicinal Chemistry and Drug Discovery, Fifth Edition, vol. I: Principles and Practice, Wiley-Interscience 1995, pp. 783-802, 784.*
Hager et al. in J Neural Transm Suppl 2007; (72):189-193 (Abstract).*
Bridges, R., et al., (2012) "System xc(-) cystine/glutamate antiporter: an update on molecular pharmacology and roles within the CNS." *Br J Pharmacol*, 165(1): 20-34.
Cui, W., et al., (2012) "Prevention of diabetic nephropathy by sulforaphane: possible role of Nrf2 upregulation and activation." *Oxid Med Cell Longev*, 2012: 821936 [12 pages].
de Haan, J.B., (2011) "Nrf2 activators as attractive therapeutics for diabetic nephropathy." *Diabetes*, 60(11): 2683-4.
Font-Llitjos, M., et al., (2007) "Slc7a9 knockout mouse is a good cystinuria model for antilithiasic pharmacological studies." *Am J Physiol Renal Physiol*, 293(3): F732-40.
Livrozet, M., et al., (2014) "An animal model of type A cystinuria due to spontaneous mutation in 129S2/SvPasCrl mice." *PLoS One*, 9(7): e102700 [8 pages].
Pohanka, M., (2013) "Alzheimer's disease and oxidative stress: A Review." *Curr Med Chem*, 21(3): 356-64.
Rimer, J.D., et al., (2010) "Crystal growth inhibitors for the prevention of L-cystine kidney stones through molecular design." *Science*, 330(6002): 337-41.
Sahota, A., et al., (2014) "Novel cystine ester mimics for the treatment of cystinuria-induced urolithiasis in a knockout mouse model." *Urology*, 84(5): 1249 e9-15. [HHS Public Access—Author manuscript—13 pages].
Sasaki, H., et al., (2002) "Electrophile response element-mediated induction of the cystine/glutamate exchange transporter gene expression." *J Biol Chem*, 277(47): 44765-71.
Shih, A.Y., et al., (2006) "Cystine/glutamate exchange modulates glutathione supply for neuroprotection from oxidative stress and cell proliferation." *J Neurosci*, 26(41): 10514-23.
Sumorok and Goldfarb (2013) "Update on cystinuria" *Curr. Opin. Nephrol. Hypertens.*, 22(4): 427-431. [HHS Public Access—Author manuscript—8 pages].
Valko, M., et al., (2007) "Free radicals and antioxidants in normal physiological functions and human disease." *Int J Biochem Cell Biol*, 39(1): p. 44-84.
Zhang, D.D., (2006) "Mechanistic studies of the Nrf2-Keap1 signaling pathway." *Drug Metab Rev*, 38(4): 769-89.

* cited by examiner

*Primary Examiner* — Dennis Heyer
(74) *Attorney, Agent, or Firm* — Tom Hunter; Weaver Austin Villeneuve & Sampson LLP

(57) ABSTRACT

In various embodiments methods and composition are provided for the treatment and/or prophylaxis of cystinuria. In certain embodiments the methods involve administering to a mammal in need thereof (e.g., identified as at risk for, or having cystinuria) an effective amount of lipoic acid and/or one or more lipoic acid derivatives.

7 Claims, 5 Drawing Sheets

LIPOIC ACID AND DERIVATIVES THEREOF FOR THE TREATMENT OF CYSTINURIA

CROSS-REFERENCE TO RELATED APPLICATIONS

This application claims benefit of and priority to U.S. Ser. No. 62/238,617, filed on Oct. 7, 2015, which is incorporated herein by reference in its entirety for all purposes.

STATEMENT OF GOVERNMENTAL SUPPORT

This invention was made with government support under Grant No. P20DK100863-02S2 awarded by the National Institutes of Health, National Institute of Diabetes and Digestive and Kidney Diseases. The Government has certain rights in this invention.

BACKGROUND

Cystinuria is a type of kidney stone disease characterized by recurrent formation of cystine-based stones. This painful condition is caused by mutations in the SLC3A1 and/or SLC7A9 gene(s), which code for the two components of the low-affinity high-capacity cystine transporter that is responsible for the reabsorption of cystine and other dibasic amino acids from the urine (Fernandez et al. (2002) *Am. J. Physiol. Renal. Physiol.* 283(3): F540-F5488; Wang et al. (2009) *Comp. Biochem. Physiol. B Biochem. Mol. Biol.* 154(1): 157-164; Calonge et al. (1994) *Nat. Genet.* 6(4): 420-425). Cystinuria patients accumulate low-soluble cystine in their urine, which then precipitates into crystals and aggregate to form painful kidney stones (Dent et al. (1965) *Br. Med. J.* 1(5432): 403-408; Dent and Senior (1955) *Br. J. Urol.* 27(4): 317-32). Cystinuria is notable because patients often generate multiple urinary stones at a high frequency of recurrence, often requiring repetitive surgical interventions to remove large stones (Mattoo and Goldfarb (2008) *Semin. Nephrol.* 28(2): 181-191).

Approximately 7% of American women and 11% of men will experience at least one kidney stone over the course of their lifetime. Kidney stones are an increasing public health problem as the prevalence of kidney stones is increasing worldwide. They are leading cause of mortality in the developing world, and medical expenditures related to stones are estimated to cause $2 billion dollars per year in the United States (Coe et al. (2005) *J. Clin. Invest.* 115(10): 2598-2608; Scales et al. (2012) *Eur. Urol.* 62(1): 160-165; Romero et al. (2010) *Rev. Urol.* 12(2-3): e86-e96). Cystinuria is an autosomal form of kidney stone disorder that affects approximately 1 out of 7,000 people} and represent approximately 1-2% of kidney stone patients and 6-7% of pediatric calculi (Palacin et al. (2001) *Curr. Opin. Genet. Dev.* 11(3): 328-335).

Much progress has been made in the development of surgical treatments aimed at removing stones from patients afflicted with kidney stones (Sumorok and Goldfarb (2013) *Curr. Opin. Nephrol. Hypertens.* 22(4): 427-431). However, there have been few advances in the understanding of the stone aggregation process and on the development of non-surgical measures that prevent recurrent stones. Our incomplete understanding of the processes that underlie urinary stone development leaves us with little paths towards the prevention of kidney stones, an important problem as 50% of kidney stone patients, and nearly all cystinuria patients, will incur repeat stone events (Chillaron et al. (2010) *Nat. Rev. Nephrol.* 6(7): 424-434).

Although the pathophysiology and genetics of cystinuria are well characterized, there has been little progress in {the development of effective interventions aimed at preventing stone recurrence. Hyperhydration (consummation of adequate fluids to result in urinary volumes greater than 3-4 liters per day) and urine alkalization (typically with potassium citrate at 6-8 tablets per day), along with a low animal protein diet, are often recommended to help to suppress cystine precipitation (Dent et al. (1965) *Br. Med. J.* 1(5432): 403-408). However, nearly all cystinuric patients require pharmaceutical interventions. Commonly prescribed medications include D-penicillamine and tiopronin (Thiola), which compete with cysteine to form the more soluble asymmetric dimers in the urine (Saravakos et al. (2014) *Urology*, 83(4): 693-699).

Yet in spite of these interventions, cystinuric patients require between 0.14-0.32 procedures per year to remove obstructive cystine stones (Ng and Streem (1999) *J. Endourol.* 13(9): 647-651; Chow and Streem (1996) *J. Urol.* 156(5): 1576-1578; Barbey et al. (2000) *J. Urol.* 163(5): 1419-1423). In addition, D-penicillamine and tiopronin are associated with serious adverse side effects which include nephrotoxicity and other kidney injury in patients whose kidneys are already compromised by recurrent stone formation (Sumorok and Goldfarb (2013) *Curr. Opin. Nephrol. Hypertens.* 22(4): 427-431; Saravakos et al. (2014) *Urology*, 83(4): 693-699; ecker (2007) Caring for Australians with Renal Impairment, *The CARI guidelines. Kidney stones: cystine stones. Nephrology (Carlton)*, 12(Suppl 1): S4-S10; Koraishy et al. (2013) *Am. J. Kidney Dis.* 62(4): 806-809). Many cystinuric patients thus resort to kidney transplants as recourse (Hoitsma et al. (1983) *JAMA* 250(5): 615; Capelli et al. (2015) *Kidney Transplantation and inborn errors of metabolism*]. *G Ital Nefrol*, 32(2)).

SUMMARY

In various embodiments methods and composition are provided for the treatment and/or prophylaxis of cystinuria. It was a surprising discovery that lipoic acid and lipoic acid derivatives can prevent the development of kidney stones associated with cystinuria and/or can slow the rate of accumulation of such stones, and/or enhance the recovery/removal of such kidney stones.

Various embodiments contemplated herein may include, but need not be limited to, one or more of the following:

Embodiment 1

A method of treating or preventing Cystinuria said method including administering to a mammal in need thereof an effective amount of lipoic acid and/or one or more lipoic acid derivatives.

Embodiment 2

The method of embodiment 1, wherein said mammal is a mammal with cystine-based kidney stones.

Embodiment 3

The method according to any one of embodiments 1-2, wherein said method is effective to slow the rate of kidney stone accumulation.

Embodiment 4

The method according to any one of embodiments 1-2, wherein said method accelerates the rate of kidney stone reduction.

Embodiment 5

The method of embodiment 1, wherein said mammal is a mammal at risk for the formation of kidney stones.

Embodiment 6

The method of embodiment 5, wherein said mammal is a mammal with a history of Cystinuria.

Embodiment 7

The method of embodiment 5, wherein said mammal is a mammal with a family history of Cystinuria.

Embodiment 8

The method of embodiment 5, wherein said mammal is a mammal with a mutation in the SLC3A1 and/or SLC7A9 gene(s).

Embodiment 9

The method according to any one of embodiments 1-8, wherein said mammal is a human.

Embodiment 10

The method according to any one of embodiments 1-8, wherein said mammal is a non-human mammal.

Embodiment 11

The method according to any one of embodiments 1-10, wherein said mammal is not diagnosed with or under treatment for cancer.

Embodiment 12

The method according to any one of embodiments 1-11, wherein said mammal is not diagnosed with or under treatment for diabetes.

Embodiment 13

The method according to any one of embodiments 1-12, wherein said mammal is not diagnosed with or under treatment for, cataracts, and/or glaucoma, and/or Wilson's disease.

Embodiment 14

The method according to any one of embodiments 1-13, wherein said mammal is not diagnosed with or under treatment for memory loss, and/or Alzheimer's disease, and/or chronic fatigue syndrome (CFS), and/or HIV/AIDS, and/or liver disease, mitochondrial disorders, and/or Lyme disease.

Embodiment 15

The method according to any one of embodiments 1-14, wherein said mammal is not diagnosed with or under treatment for a disease of the heart and/or blood vessels (e.g., atherosclerosis, and/or cardiac autonomic neuropathy, and/or cardiomyopathy).

Embodiment 16

The method according to any one of embodiments 1-15, wherein said mammal is not diagnosed with or under treatment for one or more of the following: multiple sclerosis and other chronic inflammatory diseases of the central nervous system, burning mouth syndrome, osteoporosis, and/or a skin disorder, and/or weight loss.

Embodiment 17

The method according to any one of embodiments 1-16, wherein said mammal is not diagnosed with or under treatment for one or more of the following: diabetes (glucose control), diabetic complications (neuropathy, nephropathy, cardiomyopathy, etc), insulin autoimmune syndrome, and obesity/metabolic disorder.

Embodiment 18

The method according to any one of embodiments 1-17, wherein said lipoic acid or lipoic acid derivative comprise a molecule according to Formula $$\begin{array}{c} R^1 \quad\quad R^2 \\ | \quad\quad | \\ S \quad\quad S \quad\quad\quad O \\ | \quad\quad | \quad\quad\quad \| \\ H-CH-CH_2-CH-(CH_2)_x-C-OH \end{array} \quad\quad I$$

wherein X is 0 to 16; and $R^1$ and $R^2$ are independently selected from the group consisting of an alkyl group, an acyl group, an aromatic group, an alkene group, and an alkyne group, or $R^1$ and $R^2$ are absent and the two sulfur atoms are joined to each other by a single bond.

Embodiment 19

The method of embodiment 18, wherein $R^1$ and $R^2$ are absent and the two sulfur atoms are joined to each other by a single bond.

Embodiment 20

The method of embodiment 19, wherein said lipoic acid or lipoic acid derivative has the formula:

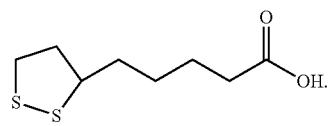 [SMILES: O=C(O)CCCCC1CCSS1]

Embodiment 21

The method of embodiment 19, wherein said lipoic acid or lipoic acid derivative has the formula:

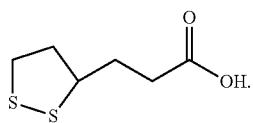

Embodiment 22

The method of embodiment 19, wherein said lipoic acid or lipoic acid derivative has the formula:

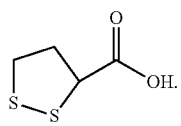

Embodiment 23

The method of embodiment 18, wherein $R^1$ and $R^2$ are the same.

Embodiment 24

The method of embodiment 18, wherein $R^1$ and $R^2$ are different.

Embodiment 25

The method according to any one of embodiments 18, 23, or 24, wherein $R^1$ and/or $R^2$ are substituted or unsubstituted alkyl groups.

Embodiment 26

The method of embodiment 25, wherein $R^1$ and/or $R^2$ are substituted alkyl groups.

Embodiment 27

The method of embodiment 26, wherein $R^1$ and $R^2$ independently alklyl substituted with a group selected from the group consisting of OH, Cl, and $NH_2$.

Embodiment 28

The method of embodiment 25, wherein $R^1$ and $R^2$ are independently selected from the group consisting of methyl, ethyl, butyl, decanyl, and 6,8-biscarbomoylmethylipoate.

Embodiment 29

The method of embodiment 25, wherein $R^1$ and $R^2$ are both methyl.

Embodiment 30

The method of embodiment 29 wherein said lipoic acid or lipoic acid derivative has the formula:

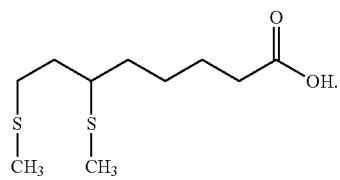

Embodiment 31

The method of embodiment 29 wherein said lipoic acid or lipoic acid derivative has the formula:

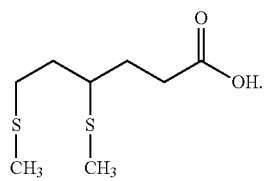

Embodiment 32

The method of embodiment 29 wherein said lipoic acid or lipoic acid derivative has the formula:

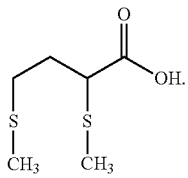

Embodiment 33

The method of embodiment 25, wherein said lipoic acid or lipoic acid derivative is 6,8-bis carbomoyl methylipoate.

Embodiment 34

The method according to any one of embodiments 18, 23, or 24, wherein $R^1$ and/or $R^2$ are acyl groups selected from the group consisting of acetyl and butaryl.

Embodiment 35

The method of embodiment 34, wherein said lipoic acid or lipoic acid derivative is bis-acetyl lipoate.

Embodiment 36

The method according to any one of embodiments 18, 23, or 24, wherein $R^1$ and/or $R^2$ are aromatic groups.

Embodiment 37

The method of embodiment 36, wherein said aromatic group is benzoyl or a benzoyl derivative.

Embodiment 38

The method of embodiment 37, wherein said lipoic acid or lipoic acid derivative is bis-benzoyl lipoate.

Embodiment 39

The method of embodiment 36, wherein said aromatic group is benzene or a benzene derivative.

Embodiment 40

The method of embodiment 39, wherein said aromatic group is a benzene derivative selected from the group consisting of toluene, and aniline.

Embodiment 41

The method according to any one of embodiments 18, 23, or 24, wherein $R^1$ and/or $R^2$ are alkene.

Embodiment 42

The method of embodiment 41, wherein $R^1$ and/or $R^2$ are selected from the group consisting of propylene, 2,3 dimethyl-2-butene, and heptane.

Embodiment 43

The method according to any one of embodiments 18, 23, or 24, wherein $R^1$ and/or $R^2$ are alkyne.

Embodiment 44

The method of embodiment, wherein said alkyne is selected from the group consisting of acetylene, propyne, and octyne.

Embodiment 45

The method according to any one of embodiments 18, 23, or 24, wherein $R^1$ and/or $R^2$ comprise thio-esters that can be oxidized to produce sulfoxides or sulfones.

Embodiment 46

The method according to any one of embodiments 18, 23, or 24, wherein $R^1$ and/or $R^2$ comprise disulfides that can be oxidized to thiosulinic or thiosulfonic acids.

Embodiment 47

The method according to any one of embodiments 1-46, wherein said lipoic acid or lipoic acid derivative includes a racemic mixture.

Embodiment 48

The method according to any one of embodiments 1-46, wherein said lipoic acid or lipoic acid derivative includes a mixture of stereoisomers enriched with the R-isomer.

Embodiment 49

The method according to any one of embodiments 1-46, wherein said lipoic acid or lipoic acid derivative includes a mixture of stereoisomers enriched with the L-isomer.

Embodiment 50

The method according to any one of embodiments 1-46, wherein said lipoic acid or lipoic acid derivative includes a substantially pure L-isomer.

Embodiment 51

The method according to any one of embodiments 1-46, wherein said lipoic acid or lipoic acid derivative includes a substantially pure R-isomer.

Embodiment 52

The method according to any one of embodiments 1-51, wherein said lipoic acid or lipoic acid derivative is formulated as a pharmaceutical formulation including the lipoic acid or lipoic acid derivative and a pharmaceutically acceptable carrier.

Embodiment 53

The method of embodiment 52, wherein said pharmaceutical formulation is a unit dosage formulation.

Embodiment 54

The method according to any one of embodiments 52-53, wherein said pharmaceutical formulation is formulated for administration via a route selected from the group consisting of isophoretic delivery, transdermal delivery, aerosol administration, administration via inhalation, oral administration, intravenous administration, and rectal administration.

Embodiment 55

The method according to any one of embodiments 1-54, wherein said lipoic acid is administered in conjunction with an alkalinizing agent.

Embodiment 56

The method of embodiment 55, wherein said alkalinizing agent includes a sodium-based alkalinizing agent.

Embodiment 57

The method of embodiment 56, wherein said alkalinizing agent is selected from the group consisting of sodium bicarbonate tablet, and sodium citrate and citric acid solution.

Embodiment 58

The method of embodiment 55, wherein said alkalinizing agent includes a potassium-based alkalinizing agent.

Embodiment 59

The method of embodiment 58, wherein said alkalinizing agent includes potassium citrate-bicarbonate tablets, slow-release potassium citrate in a wax-matrix tablet, and tripotassium citrate.

Embodiment 60

The method of embodiment 58, wherein said alkalinizing agent includes tripotassium citrate.

Embodiment 61

The method of embodiment 55, wherein said alkalinizing agent includes a acetazolamide (Diamox).

Embodiment 62

The method according to any one of embodiments 55-61, wherein said alkalinizing agent is administered at a lower dosage than would be administered if it were used alone for the treatment of cystinuria.

Embodiment 63

A pharmaceutical formulation said pharmaceutical formulation including: one or more lipoic acid or a lipoic acid derivatives according to any one of embodiments 1-51; and an alkalinizing agent.

Embodiment 64

The formulation of embodiment 63, wherein said alkalinizing agent includes a sodium-based alkalinizing agent.

Embodiment 65

The formulation of embodiment 64, wherein said alkalinizing agent is selected from the group consisting of sodium bicarbonate tablet, and sodium citrate and citric acid solution.

Embodiment 66

The formulation of embodiment 63, wherein said alkalinizing agent includes a potassium-based alkalinizing agent.

Embodiment 67

The formulation of embodiment 66, wherein said alkalinizing agent includes potassium citrate-bicarbonate tablets, slow-release potassium citrate in a wax-matrix tablet, and tripotassium citrate.

Embodiment 68

The formulation of embodiment 66, wherein said alkalinizing agent includes tripotassium citrate.

Embodiment 69

The formulation of embodiment 63, wherein said alkalinizing agent includes acetazolamide (Diamox).

Embodiment 70

The formulation according to any one of embodiments 63-69, wherein said pharmaceutical formulation is a unit dosage formulation.

Embodiment 71

The formulation according to any one of embodiments 63-70, wherein said 1 formulation is formulated for administration via a route selected from the group consisting of isophoretic delivery, transdermal delivery, aerosol administration, administration via inhalation, oral administration, intravenous administration, and rectal administration.

DEFINITIONS

The terms "subject," "individual," and "patient" may be used interchangeably and refer to humans, the as well as non-human mammals (e.g., non-human primates, canines, equines, felines, porcines, bovines, ungulates, lagomorphs, and the like). In various embodiments, the subject can be a human (e.g., adult male, adult female, adolescent male, adolescent female, male child, female child) under the care of a physician or other health worker in a hospital, as an outpatient, or other clinical context. In certain embodiments, the subject may not be under the care or prescription of a physician or other health worker.

As used herein, the phrase "a subject in need thereof" refers to a subject, as described infra, that suffers from, or is at risk for, cystinuria, in particular the formation of kidney stones associated with cystinuria.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counterions. Salts can form from or incorporate one or more deprotonated acidic groups (e.g. carboxylic acids), one or more protonated basic groups (e.g. amines), or both (e.g. zwitterions).

The term "substantially pure" or "substantially pure chiral form" when used with respect to enantiomers indicates that one particular enantiomer (e.g. an S enantiomer or an R enantiomer) is substantially free of its stereoisomer(s). In various embodiments substantially pure indicates that a particular enantiomer is at least 70%, or at least 80%, or at least 90%, or at least 95%, or at least 98%, or at least 99% of the purified compound. Methods of producing substantially pure enantiomers are well known to those of skill in the art. For example, a single stereoisomer, e.g., an enantiomer, substantially free of its stereoisomer may be obtained by resolution of the racemic mixture using a method such as formation of diastereomers using optically active resolving agents (Stereochemistry of Carbon Compounds, (1962) by E. L. Eliel, McGraw Hill; Lochmuller (1975) *J. Chromatogr.,* 113(3): 283-302). Racemic mixtures of chiral compounds can be separated and isolated by any suitable method, including, but not limited to: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. Another approach for separation of the enantiomers is to use a Diacel chiral column and elution using an organic mobile phase such as done by Chiral Technologies (www.chiraltech.com) on a fee for service basis.

The terms "coadministration" or "administration in conjunction with" or "cotreatment" when used in reference to the coadministration of a first compound (e.g., lipoic acid and/or a lipoic acid deriviative) and a second compound (e.g., an alkalinizing agen) indicates that the first compound and the second compound are administered so that there is at least some chronological overlap in the biological activity of first compound and the second compound in the organism to which they are administered. Coadministration can simultaneous administration or sequential administration. In sequential administration there may even be some substantial delay (e.g., minutes or even hours) between administration of the first compound and the second compound as long as their biological activities overlap. In certain embodiments the coadminstration is over a time frame that permits the first compound and second compound to produce an enhanced therapeutic or prophylactic effect on the organism. In certain embodiments the enhanced effect is a synergistic effect.

BRIEF DESCRIPTION OF THE DRAWINGS

FIG. 3A shows stone volume as a function of time before and after lipoic acid treatment. FIG. 3B shows the rate (absolute and normalized) of stone volume accumulation before and after lipoic acid treatment.

DETAILED DESCRIPTION

Figure 1:
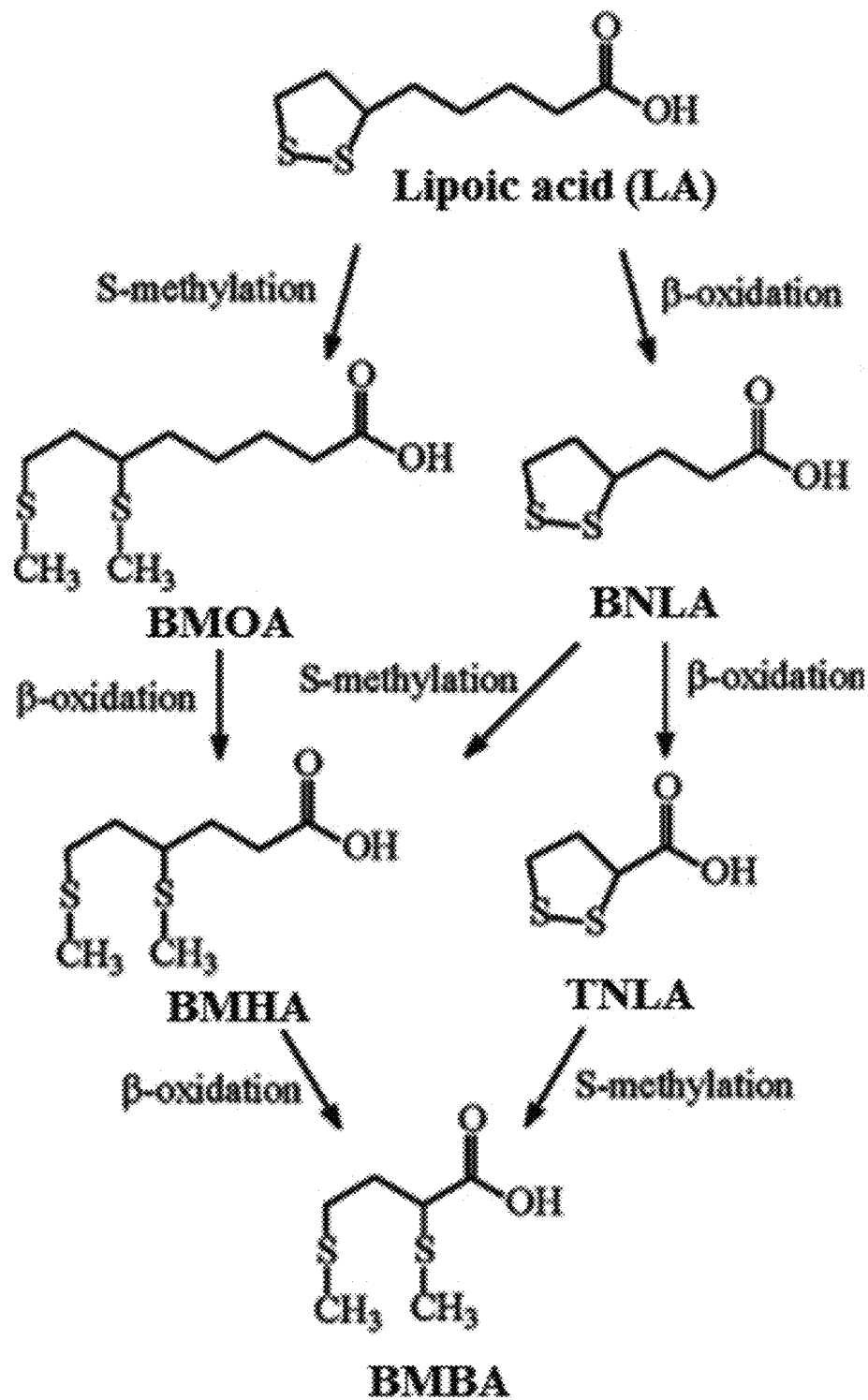
FIG. 1 shows a formula for lipoic acid and some illustrative lipoic acid derivatives.
Figure 2:
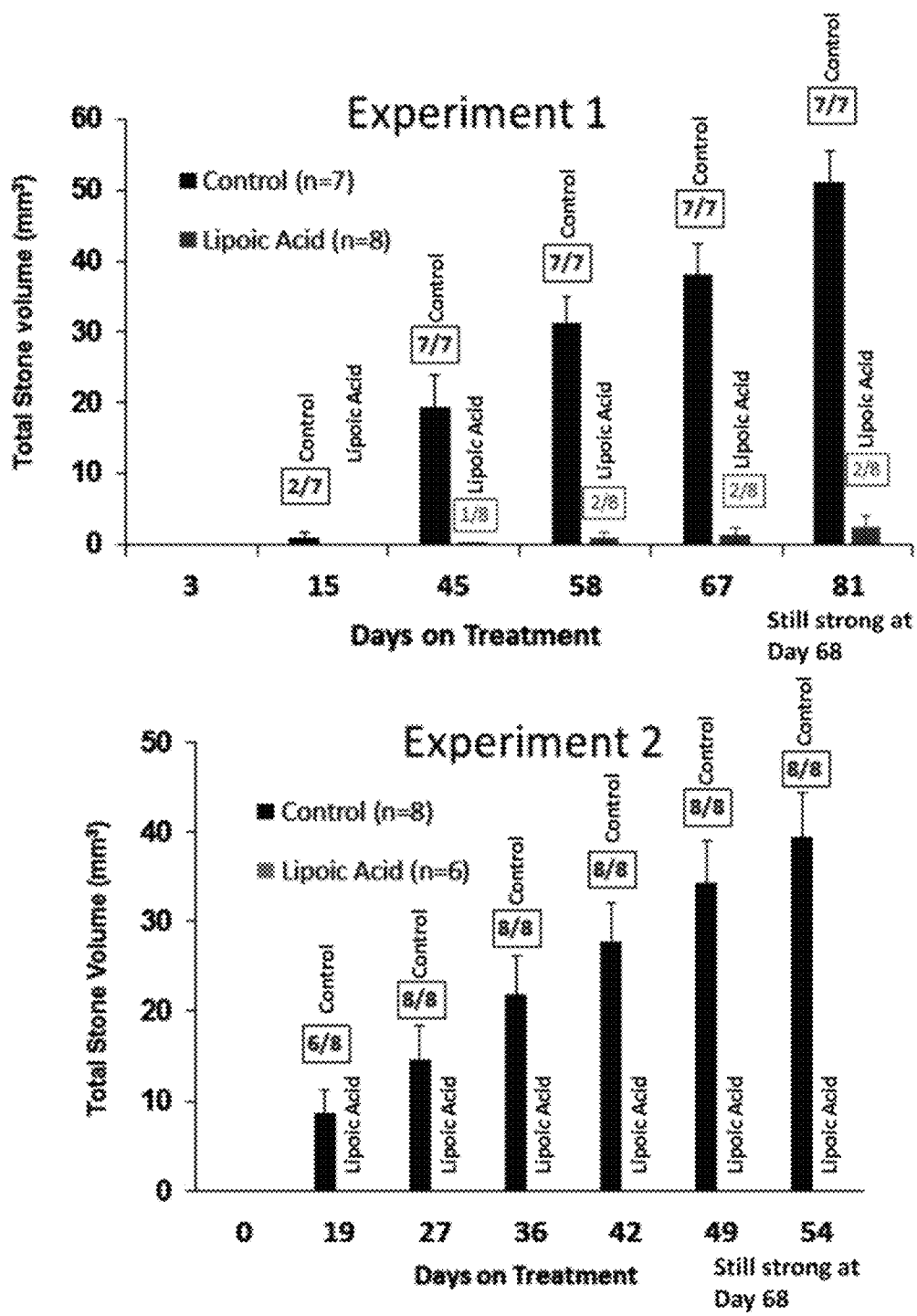
FIG. 2 shows that lipoic acid treatment prevents the development of kidney stones.
Figure 3A:
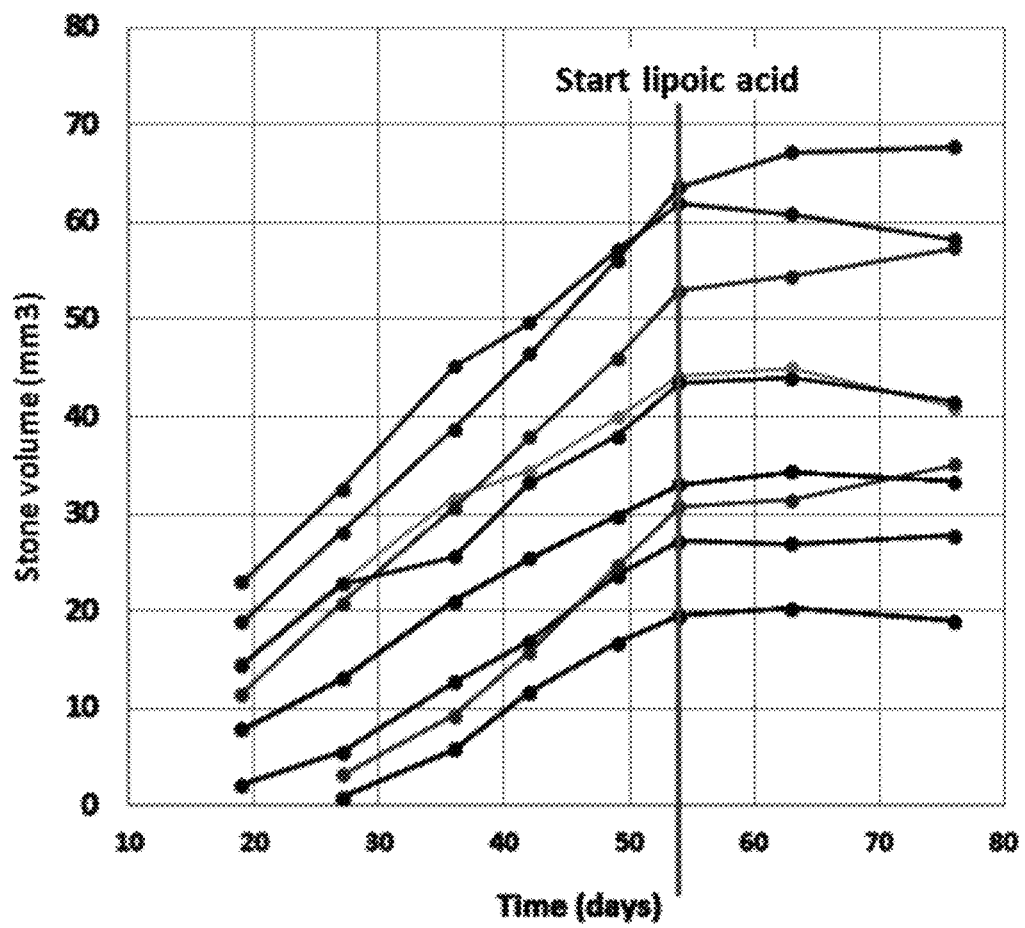
FIGS. 3A and 3B show that treatment with Lipoic Acid drastically inhibits the trajectory of stone accumulation.
Figure 3B:
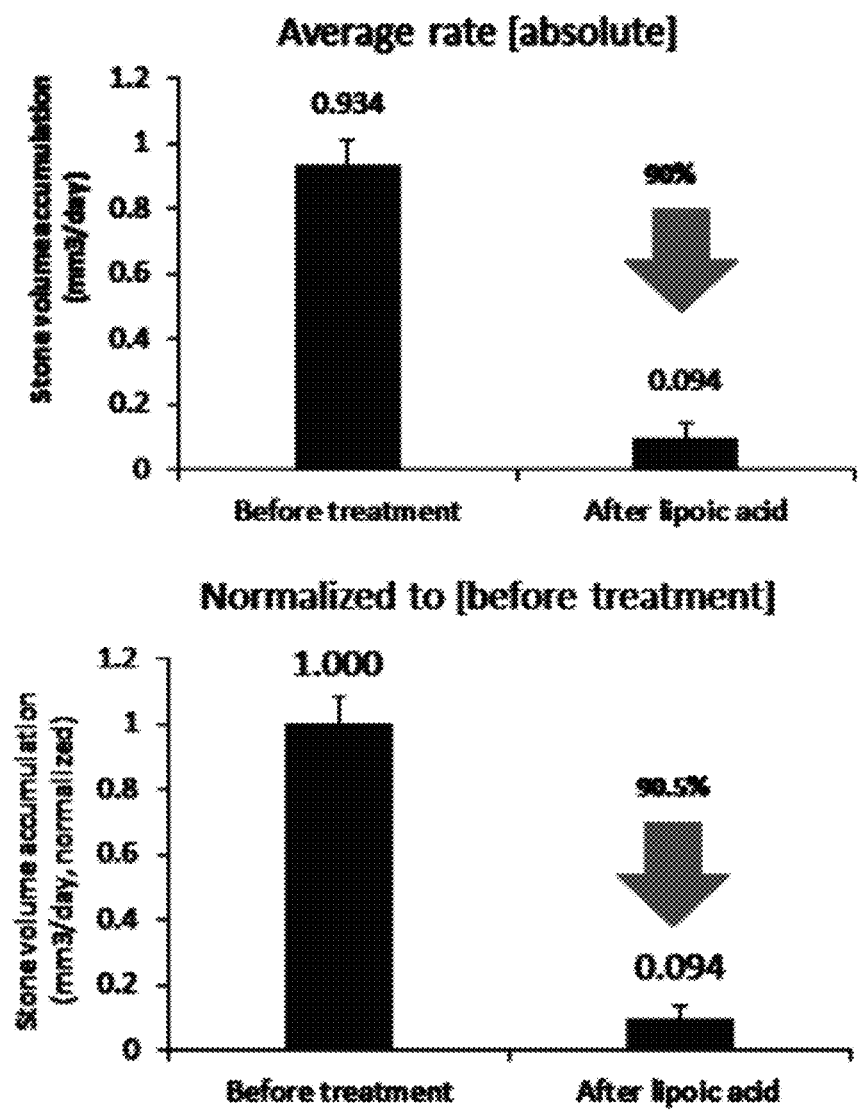
Figure 4:
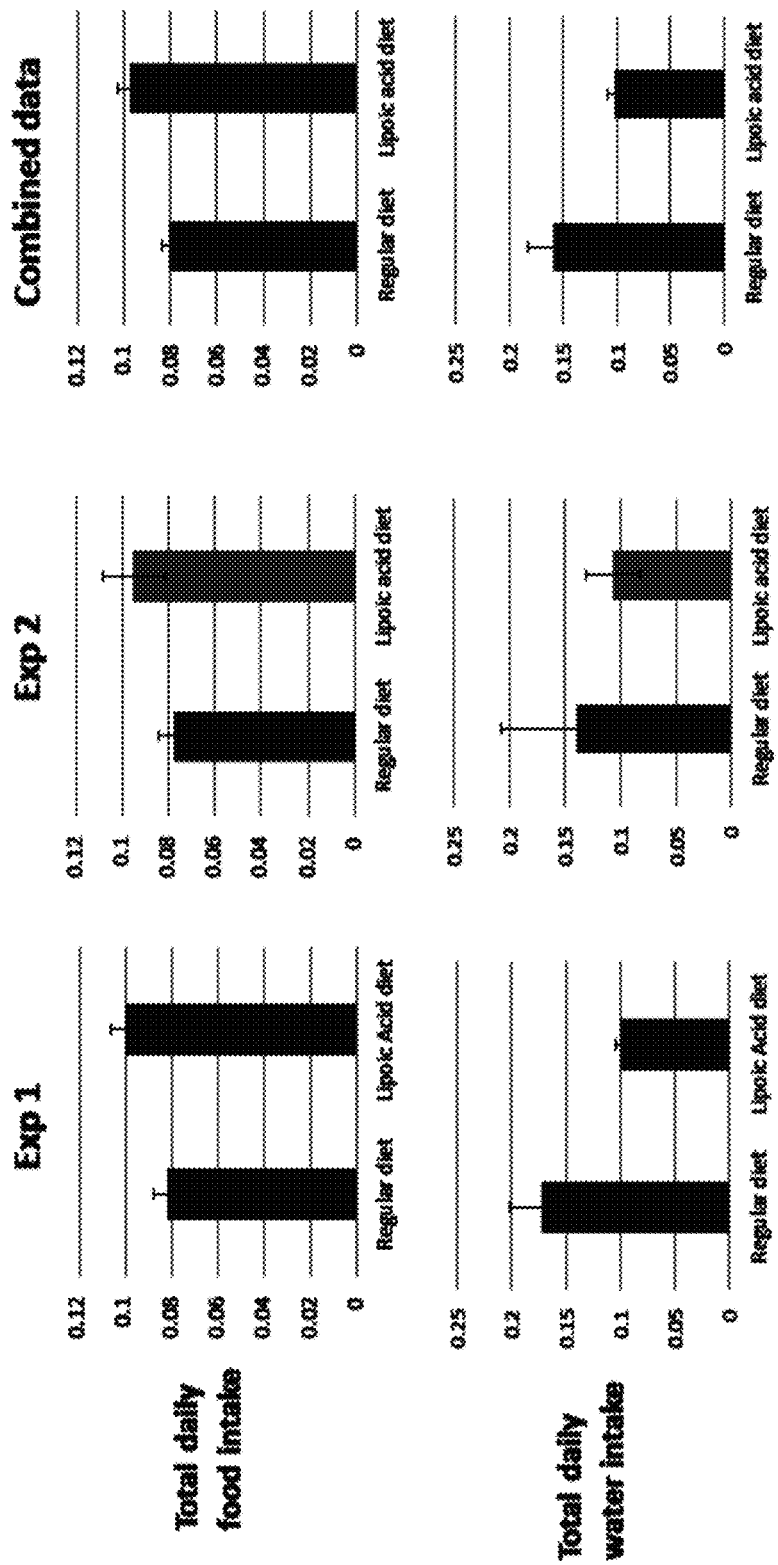
FIG. 4 shows that mice on a lipoic acid diet do not have especially altered food or water intake.

In various embodiments methods and composition are provided for the treatment and/or prophylaxis of cystinuria. It was a surprising discovery that lipoic acid and lipoic acid derivatives can prevent the development of kidney stones associated with cystinuria and/or can slow the rate of accumulation of such stones, and/or enhance the recovery/removal of such kidney stones.

Accordingly in certain embodiments the prophylactic use of lipoic acid and/or lipoic acid derivatives to prevent the formation and/or accumulation of kidney stones associated with cystinuria is contemplated. In such instances the lipoic acid and/or lipoic acid derivatives can be administered to a subject at risk for cystinuria. Such a subject can include, inter alia, a subject with a family history of cystinuria, and/or a subject with mutations in the SLC3A1 and/or SLC7A9 gene(s), and/or a subject that has a pervious history of cystinuria and associated kidney stone formation. In certain embodiments the lipoic acid and/or lipoic acid derivatives will be administered as a prophylactic pharmacologic intervention. However, in certain embodiments, the lipoic acid and/or lipoic acid derivatives can be provided as a dietary supplement. Typically the subject will be administered an amount effective to prevent the formation and/or accumulation of kidney stones associated with cystinuria.

In certain embodiments the therapeutic use of lipoic acid and/or lipoic acid derivatives to prevent the continued formation and/or accumulation of kidney stones or to reverse and eliminate the accumulation of kidney stones associated with cystinuria is contemplated. In such instances the lipoic acid and/or lipoic acid derivatives can be administered to a subject identified as having cystinuria, e.g., as having kidney stones associated with cystinuria. Typically the subject will be administered an amount effective to prevent the continued formation and/or accumulation of kidney stones and/or to reverse and eliminate the accumulation of kidney stones associated with cystinuria.

In certain embodiments the lipoic acid and/or lipoic acid derivative will be administered in conjunction with one or more other agents for the treatment and/or prevention of kidney stones associated with cyctinuria. In certain embodiments such agents include, but are not limited to alkalinizing agents. Illustrative alkalinizing agents include, but are not limited to sodium-based alkalinizing agent (e.g., sodium bicarbonate tablets, BICITRA oral solution (sodium citrate and citric acid), potassium-based alkalinizing agents (e.g., potassium citrate and citric acid (POLYCITRA-K® Crystals), potassium citrate-bicarbonate (K-Lyte tablets), slow-release potassium citrate in a wax-matrix tablet (UROCIT-K), and the like), and acetazolamide (Diamox).

In certain embodiments pharmaceutical formulations are provided that comprises lipoic acid and/or lipoic acid derivative and an alkalinizing agent. Illustrative alkalinizing agents include, but are not limited to sodium-based alkalinizing agent (e.g., sodium bicarbonate tablets, BICITRA oral solution (sodium citrate and citric acid), potassium-based alkalinizing agents (e.g., potassium citrate and citric acid (POLYCITRA-K® Crystals), potassium citrate-bicarbonate (K-Lyte tablets), slow-release potassium citrate in a wax-matrix tablet (UROCIT-K), and the like), and acetazolamide (Diamox).

Lipoic Acid and Lipoic Acid Derivatives.

As explained above, it was discovered that lipoic acid and lipoic acid derivatives can be used in the treatment of cystinuria. In particular it is demonstrated that lipoic acid can slow or stop the rate of kidney stone accumulation in cystinuria and it is believed that lipoic acid and lipoic acid derivatives can be used in the treatment and/or prophylaxis of cystinuria.

Lipoic acid well known and commercially available as are a number of lipoic acid derivatives (see, e.g., WO 2003/084532 (PCT/US2002/010761), and U.S. Pat. No. 6,331,559, which are incorporated herein for the lipoic acid derivatives shown therein. Illustrative, but non-limiting lipoic acid derivatives are shown in FIG. 1.

In certain embodiments lipoic acid or derivatives thereof comprise a molecule according to Formula I:

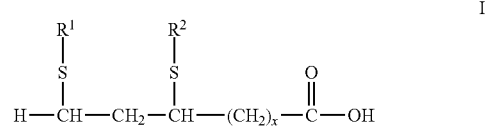

in which X is 0 to 16, or X is 0 to 8, or X is 0, or 1, or 2, or 3, or 4, or 5, or 6, or 7, or 8; and $R^1$ and $R^2$ are independently an acyl group, an aromatic group, an alkyl group, an alkene group, and alkyne group, a disulfide group, an imidoyl group, a semiacetal group, a thiester, or $R^1$ and $R^2$ are absent and the two sulfur atoms are joined to each other by a single bond (or $R^1$ and $R^2$ taken together form a single bond between the two sulfur atoms). In certain embodiments $R^1$ and $R^2$ are independently, or $R^1$ and $R^2$ are both, a substituted or an unsubstituted alkyl group, e.g., an alkyl group linked through thio-ether linkage. In certain embodiments the alkyl group comprises alkyl $C_nH_{2n}+1$ where n is 1-10, or n is 1-8, or n is 1-6, or n is 1-5, or n is 1-4, or n is 1-3, or n is 1-2, or n is 1. When the alkyl is substituted, illustrative, but non-limiting substituents include, but are not limited to OH, halogen (e.g., Cl, Fl), $NH_2$, and the like. In certain embodiments the alkyl groups include but are not limited to methyl, ethyl, propyl, butyl, pentyl, hexyl, heptyl, octyl, decanyl, and 6-8-bis carbomoyl methylipoate.

In certain embodiments $R^1$ and $R^2$ are independently, or $R^1$ and $R^2$ are both, an acyl group, e.g., an acyl group linked through a thio-ester linkage. In certain embodiments the acyl group comprises RC(O)— where R is an alkyl or aryl group. In certain embodiments the acyl groups comprises acetyl or butaryl. One illustrative, but non-limiting example of an acyl-derivatized lipoic acid is bis-acetyl lipoate.

In certain embodiments $R^1$ and $R^2$ are independently, or $R^1$ and $R^2$ are both, a substituted or unsubstituted aromatic group, e.g., an aromatic group linked through a thio-ester linkage. Illustrative aromatic groups include, but are not limited to benzoyl or benzoyl derivatives. One illustrative, but non-limiting example of a benzoyl derivatized lipoic acid is bis-benzoyl lipoate. In certain embodiments $R^1$ and $R^2$ are independently, or $R^1$ and $R^2$ are both, a substituted or unsubstituted aryl group linked through a thio-ether linkage. In certain embodiments the aromatic groups can include a benzene, a toluene, xylene, napthylene, and the like, and corresponding aryl groups include, but are not limited to phenol, tolyl, xylyl, naphthyl, and the like.

In certain embodiments $R^1$ and $R^2$ are independently, or $R^1$ and $R^2$ are both, an alkene group, e.g., an alkene linked through a thio-ether linkage. In certain embodiments the alkene may comprise alkenyl $C_nH_{2n-1}$ where n is 2-10, or 2-8, or 2-6, or 2-4. In certain embodiments the alkene includes, but is not limited to propylene, 2,3 dimethyl-2-butene, heptane, and the like.

In certain embodiments $R^1$ and $R^2$ are independently, or $R^1$ and $R^2$ are both, an alkyne group, e.g., an alkyne linked through a thio-ether linkage. In certain embodiments the alkyne may comprise alkyne $C_nH_{2n-2}$ where n is 2-10, or n is 2-8, or n is 2-6, or n is 2-4. In certain embodiments the alkyne includes, but is not limited to acetylene (ethyne), pentyne, hexyne, heptyne, octyne, nonyne, decyne, 2-butyne, propyne, and the like.

In certain embodiments the alkyl, alkene and alkyne groups can be either open chains or alicyclics. Alicyclic groups may have additions or substitutions of any of the carbons to form heterocyclics. Examples of alicylic groups include but are not limited to cyclopropane, cyclopentene, and 6,8 methyl-succinimido lipoate.

In certain embodiments the alkyl, alkene and alkyne groups can have additions on any of their carbons. Examples of additions include but are not limited to hydroxyls and amines.

In certain embodiments $R^1$ and $R^2$ are independently, or $R^1$ and $R^2$ are both, a disulfide group, e.g., a disulfide group alklyl sulfide $CH_3CH_n$—S—, where n is 0-9, or 0-8, or 0-7, or 0-6, or 0-5, or 0-4, or 0-3, or 0-2, or 0-1, or 0.

In certain embodiments $R^1$ and $R^2$ are independently, or $R^1$ and $R^2$ are both, an imidoyl group $CH3(CH2)_nC$ (=NH)—, where n is 0-9, or 0-8, or 0-7, or 0-6, or 0-5, or 0-4, or 0-3, or 0-2, or 0-1, or 0.

In certain embodiments $R^1$ and $R^2$ are independently, or $R^1$ and $R^2$ are both, a semiacetal group RCH(OH)—S—, where R is compounds with strong electron withdrawing substituents, e.g., trichloracetaldehyde, pyruvic acid, and the like.

In certain embodiments $R^1$ and $R^2$ independently, or $R^1$ and $R^2$ both, comprise thioesters that can be oxidized to produce sulfoxides or sulfones, e.g., C—S(O)—R, C—S(O) 2-R, respectively. In certain embodiments R1 and/or R2 may comprise disulfides that can be oxidized to thiosulfinnic or thiosulfonic acids, e.g., C—S(O)—S—R, and C—S(O)$_2$—S—R, respectively.

In certain embodiments the lipoic acid of is derivatized by addition of a blocking group(s) to one or both sulfhydryls. These blocking groups can take any form, including but not limited to aliphatic or aromatic organic substituents added to one or both sulfhydryls. One illustrative, but non-limiting example is diethoxycarbonylated lipoic acid.

In certain embodiments the lipoic acid derivatives include lipoic acid that has been derivatized on the thiol portion of the molecule by organic groups. Compounds are available that react specifically with thiol groups and are readily known to those of skill in the art. Examples of such thio-specific reagents include, but are not limited to N-ethylmalemide (NEM), 5,5-dithiobis (2-nitrobenZoic acid) (DNTB), p-chloromercuribenzoic acid (PCMB), ethylchloroformate, and the like. In general, thiol reactive reagents form thiethers or thioesters with the reacting thiol(s)

Yet other derivatives of lipoic acid are those in which one or both of the thiols have been replaced with a selenium molecule, a sulfur analog, or an analog in which one or both lipoic acid thiols are oxidized to sulfate or related groups.

In still other embodiments, a metal or metal salt is added to one or both sulfhydryls through a bond in which a metal or metal salt forms a covalent, or coordination or chelated complex with the thiol group(s) of the lipoic acid molecule. Such metals include, but are not limited to platinum, nickel, silver, rhodium, cadmium, gold or cobalt. Metal salts include, for example, platinum bromide, platinum chloride, platinum iodide, nickel borate, nickel boride, nickel bromide, nickel chloride, nickel iodide, nickel fluoride, silver bromate, silver bromide, silver chloride, silver fluoride, silver iodide, rhodium chloride, cadmium bromide, cadmium chloride, cadmium fluoride, cadmium iodide, gold bromide, gold chloride, gold iodide, cobalt bromide, cobalt bromide, cobalt chloride, cobalt fluoride, cobalt iodide, and the like. Such salts include various metal oxidation states such as, for example, platinum (II) chloride and platinum (IV) chloride. In various embodiments the structure of the lipoic acid-metal complex comprises (metal)$_m$(lipoic acid)$_n$ where m and n are both one, or (metal)$_m$(lipoic acid)$_n$ where m is one and n is 2.

In various embodiments the lipoic acid or lipoic acid derivative used in the methods described herein comprises α-lipoic acid. In various embodiments the lipoic acid or lipoic acid derivative used in the methods described herein comprises a compound selected from the group consisting of

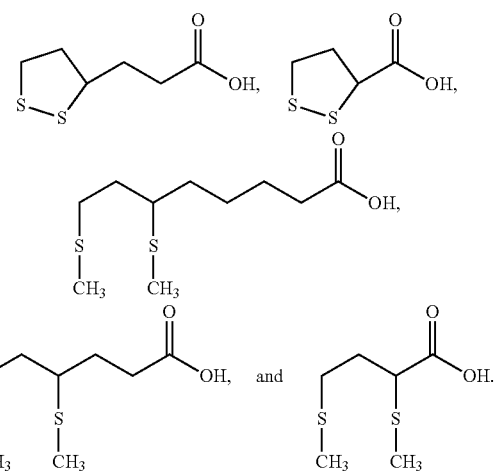

In certain embodiments the lipoic acid or lipoic acid derivative used in the methods described herein comprises α-lipoic acid. In certain embodiments the In various embodiments the lipoic acid or lipoic acid derivative used in the methods described herein comprises one or more of bis-acetyl lipoate, bis-benzoyl lipoate, 6,8-bisbenzoylmer-captooctanoic acid (bisbenzoyl lipoic acid), 8-acetylmer-capto-6-mercaptooctanoic acid (monoacetyl lipoate), 6,8-biscarbamoylmethylmercaptooctanoic acid, and 6,8-bis-[s-(n-methylsuccinimido)]mercaptooctanoic acid.

In certain embodiments In certain embodiments the lipoic acid or lipoic acid derivative used in the methods described herein comprises a compound according to formula II in U.S. Pat. No. 6,331,559, that is a compound according to the formula:

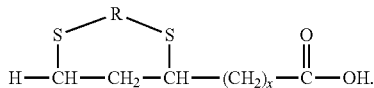

where X is 0-16, or x is 0-8, or x is 0, 1, 2, 3, 4, 5, 6, 7, or 8; and R is a covalent bond, a metal chelate, or other metal complex where the metal is not palladium.

In various embodiments lipoic acid and lipoic acid derivatives comprise optical isomers (e.g., an R- and/or an S-form). In various embodiments the lipoic acid or lipoic acid derivative is a racemate (racemic mixture). In certain embodiments the lipoic acid or lipoic acid derivative is a mixture of stereoisomers enriched with the R-isomer, or a mixture of stereoisomers enriched with the L-isomer. In certain embodiments the lipoic acid or lipoic acid derivative comprises a substantially pure L-isomer. In certain embodiments the lipoic acid or lipoic acid derivative comprises a substantially pure L-isomer.

Pharmaceutical Formulations.

In certain embodiments one or more lipoic acid or lipoic acid derivatives described herein, or a tautomer(s) or stereoisomer(s) thereof, or pharmaceutically acceptable salts or solvates thereof or a prodrug thereof are administered to a mammal in need thereof, e.g., to a mammal at risk for or suffering from cystinuria. In certain embodiments the lipoic acid and/or lipoic acid derivatives are administered to prevent or delay the onset acute cystinuria, e.g., to prevent, slow, or delay the development of kidney stones, in particular, cysteine-based stones. Accordingly, in certain embodiments, the lipoic acid and/or lipoic acid derivatives are administered to a subject at risk for cystinuria. Such subjects include, but are not limited to, subjects with a family history of cystinuria, and/or subjects that have had previous occurrences of cystinuria. In certain embodiments the lipoic acid and/or lipoic acid derivatives are administered for the treatment of cystinuria, e.g., to slow or stop the accumulation of kidney stones or to enhance the reduction and/or elimination of such kidney stones. Accordingly, in certain embodiments, the lipoic acid and/or lipoic acid derivatives are administered to a subject identified (e.g., diagnosed) as having cystinuria.

The lipoic acid and/or lipoic acid derivatives can be administered in the "native" form or, if desired, in the form of salts, esters, amides, prodrugs, derivatives, and the like, provided the salt, ester, amide, prodrug or derivative is suitable pharmacologically, i.e., effective in the present method(s). Salts, esters, amides, prodrugs and other derivatives of the the lipoic acid and/or lipoic acid derivatives can be prepared using standard procedures known to those skilled in the art of synthetic organic chemistry and described, for example, by March (1992) *Advanced Organic Chemistry; Reactions, Mechanisms and Structure*, 4th Ed. N.Y. Wiley-Interscience, and as described above.

For example, a pharmaceutically acceptable salt can be prepared for the lipoic acid and/or lipoic acid derivative(s). A pharmaceutically acceptable salt is any salt that retains the activity of the parent compound and does not impart any deleterious or untoward effect on the subject to which it is administered and in the context in which it is administered. The term pharmaceutical salt is used to refer to an ionisable drug that has been combined with a counter-ion to form a neutral complex. Converting a drug into a salt through this process can increase its chemical stability, render the complex easier to administer and allow manipulation of the agent's pharmacokinetic profile. Salt selection is now a common standard operation performed with small ionisable molecules during drug development, and in many cases the drug salts display preferential properties as compared with the parent molecule.

Methods of formulating pharmaceutically active agents as salts, esters, amide, prodrugs, and the like are well known to those of skill in the art. The pharmaceutically acceptable salt is typically generated upon the neutralization of an acidic or basic pharmaceutical salt. Pharmaceutical salts include both ionic and covalent salts.

By way of illustration, salts can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the active agents herein include halide salts, such as may be prepared using hydrochloric or hydrobromic acids.

Conversely, basic salts can be prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

For the preparation of salt forms of basic drugs, the pKa of the counterion is preferably at least about 2 pH units lower than the pKa of the drug. Similarly, for the preparation of salt forms of acidic drugs, the pKa of the counterion is preferably at least about 2 pH units higher than the pKa of the drug. This permits the counterion to bring the solution's pH to a level lower than the $pH_{max}$ to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (i.e., break down into the individual entities of drug and counterion) in an aqueous environment.

Preferably, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

Preparation of esters typically involves functionalization of hydroxyl and/or carboxyl groups that are present within the molecular structure of the lipoic acid and/or lipoic acid derivative. In certain embodiments, the esters are typically acyl-substituted derivatives of free alcohol groups, i.e., moieties that are derived from carboxylic acids of the formula RCOOH where R is alky, and typically is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

In various embodiments, the lipoic acid and/or lipoic acid derivative(s) identified herein are useful for parenteral administration, topical administration, oral administration, nasal administration (or otherwise inhaled), rectal administration, or local administration, such as by aerosol or transdermally, for prophylactic and/or therapeutic treatment of one or more of the pathologies/indications described herein (e.g., pathologies characterized by excess amyloid plaque formation and/or deposition or undesired amyloid or pre-amyloid processing).

In various embodiments the lipoic acid and/or lipoic acid derivative(s) described herein can also be combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers.

Other physiologically acceptable compounds, particularly of use in the preparation of tablets, capsules, gel caps, and the like include, but are not limited to binders, diluent/fillers, disintegrants, lubricants, suspending agents, and the like.

In certain embodiments, to manufacture an oral dosage form (e.g., a tablet), an excipient (e.g., lactose, sucrose, starch, mannitol, etc.), an optional disintegrator (e.g. calcium carbonate, carboxymethylcellulose calcium, sodium starch glycollate, crospovidone etc.), a binder (e.g. alpha-starch, gum arabic, microcrystalline cellulose, carboxymethylcellulose, polyvinylpyrrolidone, hydroxypropylcellulose, cyclodextrin, etc.), and an optional lubricant (e.g., talc, magnesium stearate, polyethylene glycol 6000, etc.), for instance, are added to the lipoic acid and/or lipoic acid derivative(s) and the resulting composition is compressed.

Where necessary the compressed product is coated, e.g., using known methods for masking the taste or for enteric dissolution or sustained release. Suitable coating materials include, but are not limited to ethyl-cellulose, hydroxymethylcellulose, POLYOX®yethylene glycol, cellulose acetate phthalate, hydroxypropylmethylcellulose phthalate, and Eudragit (Rohm & Haas, Germany; methacrylic-acrylic copolymer).

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physiochemical characteristics of the active agent(s).

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectables, implantable sustained-release formulations, mucoadherent films, topical varnishes, lipid complexes, etc.

Pharmaceutical compositions comprising the lipoic acid and/or lipoic acid derivative(s) described herein can be manufactured by means of conventional mixing, dissolving, granulating, dragee-making, levigating, emulsifying, encapsulating, entrapping or lyophilizing processes. Pharmaceutical compositions can be formulated in a conventional manner using one or more physiologically acceptable carriers, diluents, excipients or auxiliaries that facilitate processing of the active agent(s) into preparations that can be used pharmaceutically. Proper formulation is dependent upon the route of administration chosen.

In certain embodiments, the lipoic acid and/or lipoic acid derivative(s) described herein are formulated for oral administration. For oral administration, suitable formulations can be readily formulated by combining the active agent(s) with pharmaceutically acceptable carriers suitable for oral delivery well known in the art. Such carriers enable the active agent(s) described herein to be formulated as tablets, pills, dragees, caplets, lizenges, gelcaps, capsules, liquids, gels, syrups, slurries, suspensions and the like, for oral ingestion by a patient to be treated. For oral solid formulations such as, for example, powders, capsules and tablets, suitable excipients can include fillers such as sugars (e.g., lactose, sucrose, mannitol and sorbitol), cellulose preparations (e.g., maize starch, wheat starch, rice starch, potato starch, gelatin, gum tragacanth, methyl cellulose, hydroxypropylmethylcellulose, sodium carboxymethylcellulose), synthetic polymers (e.g., polyvinylpyrrolidone (PVP)), granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques. The preparation of enteric-coated particles is disclosed for example in U.S. Pat. Nos. 4,786,505 and 4,853,230.

For administration by inhalation, the the lipoic acid and/or lipoic acid derivative(s) are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g. gelatin for use in an inhaler or insufflator may be formulated containing a powder mix of the compound and a suitable powder base such as lactose or starch.

In various embodiments the lipoic acid and/or lipoic acid derivative(s) can be formulated in rectal or vaginal compositions such as suppositories or retention enemas, e.g., containing conventional suppository bases such as cocoa butter or other glycerides. Methods of formulating active agents for rectal or vaginal delivery are well known to those of skill in the art (see, e.g., Allen (2007) *Suppositories*, Pharmaceutical Press) and typically involve combining the active agents with a suitable base (e.g., hydrophilic (PEG), lipophilic materials such as cocoa butter or Witepsol W45, amphiphilic materials such as Suppocire AP and polyglycolized glyceride, and the like). The base is selected and compounded for a desired melting/delivery profile.

For topical administration the lipoic acid and/or lipoic acid derivative(s) described herein can be formulated as solutions, gels, ointments, creams, suspensions, and the like as are well-known in the art.

In certain embodiments the lipoic acid and/or lipoic acid derivative(s) described herein are formulated for systemic administration (e.g., as an injectable) in accordance with standard methods well known to those of skill in the art. Systemic formulations include, but are not limited to, those designed for administration by injection, e.g. subcutaneous, intravenous, intramuscular, intrathecal or intraperitoneal injection, as well as those designed for transdermal, transmucosal oral or pulmonary administration. For injection, the active agents described herein can be formulated in aqueous solutions, preferably in physiologically compatible buffers such as Hanks solution, Ringer's solution, or physiological saline buffer and/or in certain emulsion formulations. The solution(s) can contain formulatory agents such as suspending, stabilizing and/or dispersing agents. In certain embodiments the active agent(s) can be provided in powder form for constitution with a suitable vehicle, e.g., sterile pyrogen-free water, before use. For transmucosal administration, and/or for blood/brain barrier passage, penetrants appropriate to the barrier to be permeated can be used in the formulation. Such penetrants are generally known in the art. Injectable formulations and inhalable formulations are generally provided as a sterile or substantially sterile formulation.

In addition to the formulations described previously, the lipoic acid and/or lipoic acid derivative(s) may also be formulated as a depot preparations. Such long acting formulations can be administered by implantation (for example subcutaneously or intramuscularly) or by intramuscular injection. Thus, for example, the active agent(s) may be formulated with suitable polymeric or hydrophobic materials (for example as an emulsion in an acceptable oil) or ion exchange resins, or as sparingly soluble derivatives, for example, as a sparingly soluble salt.

In certain embodiments the lipoic acid and/or lipoic acid derivative(s) described herein can also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one illustrative embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

Alternatively, other pharmaceutical delivery systems can be employed. For example, liposomes, emulsions, and microemulsions/nanoemulsions are well known examples of delivery vehicles that may be used to protect and deliver pharmaceutically active compounds. Certain organic solvents such as dimethylsulfoxide also can be employed, although usually at the cost of greater toxicity.

In certain embodiments the lipoic acid and/or lipoic acid derivative(s) are formulated in a nanoemulsion. Nanoemulsions include, but are not limited to oil in water (O/W) nanoemulsions, and water in oil (W/O) nanoemulsions. Nanoemulsions can be defined as emulsions with mean droplet diameters ranging from about 20 to about 1000 nm. Usually, the average droplet size is between about 20 nm or 50 nm and about 500 nm. The terms sub-micron emulsion (SME) and mini-emulsion are used as synonyms.

Illustrative oil in water (O/W) nanoemulsions include, but are not limited to: Surfactant micelles—micelles composed of small molecules surfactants or detergents (e.g., SDS/PBS/2-propanol); Polymer micelles—micelles composed of polymer, copolymer, or block copolymer surfactants (e.g., Pluronic L64/PBS/2-propanol); Blended micelles—micelles in which there is more than one surfactant component or in which one of the liquid phases (generally an alcohol or fatty acid compound) participates in the formation of the micelle (e.g., octanoic acid/PBS/EtOH); Integral micelles—blended micelles in which the active agent(s) serve as an auxiliary surfactant, forming an integral part of the micelle; and Pickering (solid phase) emulsions—emulsions in which the active agent(s) are associated with the exterior of a solid nanoparticle (e.g., polystyrene nanoparticles/PBS/no oil phase).

Illustrative water in oil (W/O) nanoemulsions include, but are not limited to: Surfactant micelles—micelles composed of small molecules surfactants or detergents (e.g., dioctyl sulfosuccinate/PBS/2-propanol, isopropylmyristate/PBS/2-propanol, etc.); Polymer micelles—micelles composed of polymer, copolymer, or block copolymer surfactants (e.g., PLURONIC® L121/PBS/2-propanol); Blended micelles—micelles in which there is more than one surfactant component or in which one of the liquid phases (generally an alcohol or fatty acid compound) participates in the formation of the micelle (e.g., capric/caprylic diglyceride/PBS/EtOH); Integral micelles—blended micelles in which the active agent(s) serve as an auxiliary surfactant, forming an integral part of the micelle (e.g., active agent/PBS/polypropylene glycol); and Pickering (solid phase) emulsions—emulsions in which the active agent(s) are associated with the exterior of a solid nanoparticle (e.g., chitosan nanoparticles/no aqueous phase/mineral oil).

As indicated above, in certain embodiments the nanoemulsions comprise one or more surfactants or detergents. In some embodiments the surfactant is a non-anionic detergent (e.g., a polysorbate surfactant, a polyoxyethylene ether, etc.). Surfactants that find use in the present invention include, but are not limited to surfactants such as the TWEEN®, TRITON®, and TYLOXAPOL® families of compounds.

In certain embodiments the emulsions further comprise one or more cationic halogen containing compounds, including but not limited to, cetylpyridinium chloride. In still further embodiments, the compositions further comprise one or more compounds that increase the interaction ("interaction enhancers") of the composition with microorganisms (e.g., chelating agents like ethylenediaminetetraacetic acid, or ethylenebis(oxyethylenenitrilo)tetraacetic acid in a buffer).

In some embodiments, the nanoemulsion further comprises an emulsifying agent to aid in the formation of the emulsion. Emulsifying agents include compounds that aggregate at the oil/water interface to form a kind of continuous membrane that prevents direct contact between two adjacent droplets. Certain embodiments of the present invention feature oil-in-water emulsion compositions that may readily be diluted with water to a desired concentration without impairing their anti-pathogenic properties.

In addition to discrete oil droplets dispersed in an aqueous phase, certain oil-in-water emulsions can also contain other lipid structures, such as small lipid vesicles (e.g., lipid spheres that often consist of several substantially concentric lipid bilayers separated from each other by layers of aqueous phase), micelles (e.g., amphiphilic molecules in small clusters of 50-200 molecules arranged so that the polar head groups face outward toward the aqueous phase and the apolar tails are sequestered inward away from the aqueous phase), or lamellar phases (lipid dispersions in which each particle consists of parallel amphiphilic bilayers separated by thin films of water).

These lipid structures are formed as a result of hydrophobic forces that drive apolar residues (e.g., long hydrocarbon chains) away from water. The above lipid preparations can generally be described as surfactant lipid preparations (SLPs). SLPs are minimally toxic to mucous membranes and are believed to be metabolized within the small intestine (see e.g., Hamouda et al., (1998) J. Infect. Disease 180: 1939).

In certain embodiments the emulsion comprises a discontinuous oil phase distributed in an aqueous phase, a first component comprising an alcohol and/or glycerol, and a second component comprising a surfactant or a halogen-containing compound. The aqueous phase can comprise any type of aqueous phase including, but not limited to, water (e.g., dionized water, distilled water, tap water) and solutions (e.g., phosphate buffered saline solution or other buffer systems). The oil phase can comprise any type of oil including, but not limited to, plant oils (e.g., soybean oil, avocado oil, flaxseed oil, coconut oil, cottonseed oil, squalene oil, olive oil, canola oil, corn oil, rapeseed oil, safflower oil, and sunflower oil), animal oils (e.g., fish oil), flavor oil, water insoluble vitamins, mineral oil, and motor oil. In certain embodiments, the oil phase comprises 30-90 vol % of the oil-in-water emulsion (e.g., constitutes 30-90% of the total volume of the final emulsion), more preferably 50-80%. The formulations need not be limited to particular surfactants, however in certain embodiments, the surfactant is a polysorbate surfactant (e.g., TWEEN 20®, TWEEN 40®, TWEEN 60®, and TWEEN 80®), a pheoxypolyethoxyethanol (e.g., TRITON® X-100, X-301, X-165, X-102, and X-200, and TYLOXAPOL®), or sodium dodecyl sulfate, and the like.

In certain embodiments a halogen-containing component is present. the nature of the halogen-containing compound, in some embodiments the halogen-containing compound comprises a chloride salt (e.g., NaCl, KCl, etc.), a cetylpyridinium halide, a cetyltrimethylammonium halide, a cetyldimethylethylammonium halide, a cetyldimethylbenzylammonium halide, a cetyltributylphosphonium halide, dodecyltrimethylammonium halides, tetradecyltrimethylammonium halides, cetylpyridinium chloride, cetyltrimethylammonium chloride, cetylbenzyldimethylammonium chloride, cetylpyridinium bromide, cetyltrimethylammonium bromide, cetyldimethylethylammonium bromide, cetyltributylphosphonium bromide, dodecyltrimethylammonium bromide, tetradecyltrimethylammonium bromide, and the like In certain embodiments the emulsion comprises a quaternary ammonium compound. Quaternary ammonium compounds include, but are not limited to, N-alkyldimethyl benzyl ammonium saccharinate, 1,3,5-Triazine-1,3,5(2H, 4H,6H)-triethanol; 1-Decanaminium, N-decyl-N,N-dimethyl-, chloride (or) Didecyl dimethyl ammonium chloride; 2-(2-(p-(Diisobuyl)cresosxy)ethoxy)ethyl dimethyl benzyl ammonium chloride; 2-(2-(p-(Diisobutyl)phenoxy)ethoxy) ethyl dimethyl benzyl ammonium chloride; alkyl 1 or 3 benzyl-1-(2-hydroxethyl)-2-imidazolinium chloride; alkyl bis(2-hydroxyethyl)benzyl ammonium chloride; alkyl dimethyl benzyl ammonium chloride; alkyl dimethyl 3,4-dichlorobenzyl ammonium chloride (100% C12); alkyl dimethyl 3,4-dichlorobenzyl ammonium chloride (50% C14, 40% C12, 10% C16); alkyl dimethyl 3,4-dichlorobenzyl ammonium chloride (55% C14, 23% C12, 20% C16); alkyl dimethyl benzyl ammonium chloride; alkyl dimethyl benzyl ammonium chloride (100% C14); alkyl dimethyl benzyl ammonium chloride (100% C16); alkyl dimethyl benzyl ammonium chloride (41% C14, 28% C12); alkyl dimethyl benzyl ammonium chloride (47% C12, 18% C14); alkyl dimethyl benzyl ammonium chloride (55% C16, 20% C14); alkyl dimethyl benzyl ammonium chloride (58% C14, 28% C16); alkyl dimethyl benzyl ammonium chloride (60% C14, 25% C12); alkyl dimethyl benzyl ammonium chloride (61% C11, 23% C14); alkyl dimethyl benzyl ammonium chloride (61% C12, 23% C14); alkyl dimethyl benzyl ammonium chloride (65% C12, 25% C14); alkyl dimethyl benzyl ammonium chloride (67% C12, 24% C14); alkyl dimethyl benzyl ammonium chloride (67% C12, 25% C14); alkyl dimethyl benzyl ammonium chloride (90% C14, 5% C12); alkyl dimethyl benzyl ammonium chloride (93% C14, 4% C12); alkyl dimethyl benzyl ammonium chloride (95% C16, 5% C18); alkyl dimethyl benzyl ammonium chloride (and) didecyl dimethyl ammonium chloride; alkyl dimethyl benzyl ammonium chloride (as in fatty acids); alkyl dimethyl benzyl ammonium chloride (C12-C16); alkyl dimethyl benzyl ammonium chloride (C12-C18); alkyl dimethyl benzyl and dialkyl dimethyl ammonium chloride; alkyl dimethyl dimethybenzyl ammonium chloride; alkyl dimethyl ethyl ammonium bromide (90% C14, 5% C16, 5% C12); alkyl dimethyl ethyl ammonium bromide (mixed alkyl and alkenyl groups as in the fatty acids of soybean oil); alkyl dimethyl ethylbenzyl ammonium chloride; alkyl dimethyl ethylbenzyl ammonium chloride (60% C14); alkyl dimethyl isoproylbenzyl ammonium chloride (50% C12, 30% C14, 17% C16, 3% C18); alkyl trimethyl ammonium chloride (58% C18, 40% C16, 1% C14, 1% C12); alkyl trimethyl ammonium chloride (90% C18, 10% C16); alkyldimethyl (ethylbenzyl) ammonium chloride (C12-18); Di-(C8-10)-alkyl dimethyl ammonium chlorides; dialkyl dimethyl ammonium chloride; dialkyl dimethyl ammonium chloride; dialkyl dimethyl ammonium chloride; dialkyl methyl benzyl ammonium chloride; didecyl dimethyl ammonium chloride; diisodecyl dimethyl ammonium chloride; dioctyl dimethyl ammonium chloride; dodecyl bis(2-hydroxyethyl) octyl hydrogen ammonium chloride; dodecyl dimethyl benzyl ammonium chloride; dodecylcarbamoyl methyl dimethyl benzyl ammonium chloride; heptadecyl hydroxyethylimidazolinium chloride; hexahydro-1,3,5-thris(2-hydroxyethyl)-s-triazine; myristalkonium chloride (and) Quat RNIUM 14; N,N-Dimethyl-2-hydroxypropylammonium chloride polymer; n-alkyl dimethyl benzyl ammonium chloride; n-alkyl dimethyl ethylbenzyl ammonium chloride; n-tetradecyl dimethyl benzyl ammonium chloride monohydrate; octyl decyl dimethyl ammonium chloride; octyl dodecyl dimethyl ammonium chloride; octyphenoxyethoxyethyl dimethyl benzyl ammonium chloride; oxydiethylenebis (alkyl dimethyl ammonium chloride); quaternary ammonium compounds, dicoco alkyldimethyl, chloride; trimethoxysily propyl dimethyl octadecyl ammonium chloride; trimethoxysilyl quats, trimethyl dodecylbenzyl ammonium chloride; n-dodecyl dimethyl ethylbenzyl ammonium chloride; n-hexadecyl dimethyl benzyl ammonium chloride; n-tetradecyl dimethyl benzyl ammonium chloride; n-tetradecyl dimethyl ethylbenzyl ammonium chloride; and n-octadecyl dimethyl benzyl ammonium chloride.

Nanoemulsion formulations and methods of making such are well known to those of skill in the art and described for example in U.S. Pat. Nos. 7,476,393, 7,468,402, 7,314,624, 6,998,426, 6,902,737, 6,689,371, 6,541,018, 6,464,990, 6,461,625, 6,419,946, 6,413,527, 6,375,960, 6,335,022, 6,274,150, 6,120,778, 6,039,936, 5,925,341, 5,753,241, 5,698,219, and 5,152,923 and in Fanun et al. (2009) Microemulsions: Properties and Applications (Surfactant Science), CRC Press, Boca Ratan Fla.

In certain embodiments, one or more of the lipoic acid and/or lipoic acid derivative(s) described herein can be provided as a "concentrate", e.g., in a storage container (e.g., in a premeasured volume) ready for dilution, or in a soluble capsule ready for addition to a volume of water, alcohol, hydrogen peroxide, or other diluent.

EXAMPLES

The following examples are offered to illustrate, but not to limit the claimed invention.

Example 1

Lipoic Acid and the Prevention of Kidney Stones Associated with Cystinuria

FIG. 2 Experiment

A genetic mouse model of cystinuria was used to study the formation of cystine urinary stones. Mice lacking the gene Slc3a1 (Slc3a1$^{-/-}$) were fed a diet supplemented with 0.5% (±)-α-lipoic acid and evaluated for the formation of cystine stones using micro-computed tomography (μCT). Lipoic acid treatment effectively prevented the formation of cystine stones in most of the cystinuric mice, as only 2 out of 8 mice developed cystine stones in comparison to non-treated mice on a standard diet, all of which (7/7) formed stones early on in the treatment study. On average, mice treated with lipoic acid developed much smaller cystine stones (mm$^3$). This experiment was repeated again (Experiment 2) with similar results; none (0 out of 6) of the lipoic acid treated cystinuric mice developed stones while all control, non-treated mice (8 out of 8) had developed urinary stones had developed stones by day 27 of the study. The results of these duplicate experiments demonstrate that lipoic acid effectively prevented formation of urinary cystine stones in mice.

FIG. 3 Experiment

To evaluate the effect of lipoic acid on cystine urinary stone growth, stone development was tracked by microcomputed tomography (μCT) in Slc3a1$^{-/-}$ mice fed a standard diet. On day 54 of the study, the mice were switched onto a diet supplemented with 0.5% (±)-α-lipoic acid. Lipoic acid effectively decreased the rate of stone volume accumulation (mm$^3$/day) in these mice by 90%.

FIG. 4 Experiment

Real time food and water intake was measured in Slc3a1$^{-/-}$ mice treated with 0.5% (±)-α-lipoic acid supplemented diet by group housing in metabolic cages. Mice were acclimated to the metabolic cage environment for 3 days and then evaluated for food and water intake for the subsequent 3 days. Lipoic acid did not especially alter light cycle, dark cycle, or total food or water intake in Slc3a1$^{-/-}$ mice compared to mice fed a standard diet.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating or preventing Cystinuria said method comprising administering to a mammal in need thereof an effective amount of lipoic acid, wherein said mammal in need thereof is a mammal with cystinuria, and/or a mammal selected from the group consisting of a mammal with a family history of cystinuria, a mammal with mutations in the SLC3A1 and/or SLC7A9 gene(s), and a subject that has a previous history of cystinuria and associated kidney stone formation.

2. The method of claim 1, wherein said mammal is a mammal with cystine-based kidney stones.

3. The method of claim 1, wherein said mammal is a mammal selected from the group consisting of a mammal with a family history of cystinuria, a mammal with mutations in the SLC3A1 and/or SLC7A9 gene(s), and a subject that has a previous history of cystinuria and associated kidney stone formation.

4. The method of claim 1, wherein said lipoic acid is administered in conjunction with an alkalinizing agent.

5. The method of claim 4, wherein said alkalinizing agent comprises an agent selected from the group consisting of a sodium-based alkalinizing agent, a potassium-based alkalinizing agent, and acetazolamide.

6. The method of claim 5, wherein:
said alkalinizing agent is selected from the group consisting of sodium bicarbonate tablet, and sodium citrate and citric acid solution; or said alkalinizing agent is selected from the group consisting of a potassium citrate-bicarbonate tablet, a slow-release potassium citrate in a wax-matrix tablet, and tripotassium citrate.

7. The method of claim 4, wherein said alkalinizing agent is administered at a lower dosage than would be administered if it were used alone for the treatment of cystinuria.

* * * * *